(12) United States Patent
Helmer (10) Patent No.: US 10,960,146 B2
(45) Date of Patent: Mar. 30, 2021

(54) DRUG DELIVERY DEVICE WITH CONTROLLED NEEDLE SHIELD AND COVER SLEEVE

(71) Applicant: Sanofi-Aventis Deutschland GMBH, Frankfurt am Main (DE)

(72) Inventor: Michael Helmer, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 178 days.

(21) Appl. No.: 16/317,016

(22) PCT Filed: Jul. 12, 2017

(86) PCT No.: PCT/EP2017/067510
§ 371 (c)(1),
(2) Date: Jan. 10, 2019

(87) PCT Pub. No.: WO2018/011256
PCT Pub. Date: Jan. 18, 2018

(65) Prior Publication Data
US 2019/0290859 A1   Sep. 26, 2019

(30) Foreign Application Priority Data

Jul. 14, 2016 (EP) .................................... 16179492

(51) Int. Cl.
*A61M 5/32* (2006.01)
*A61M 5/46* (2006.01)
*A61M 5/24* (2006.01)

(52) U.S. Cl.
CPC ............ *A61M 5/3275* (2013.01); *A61M 5/24* (2013.01); *A61M 5/3202* (2013.01);
(Continued)

(58) Field of Classification Search
CPC ........ A61M 5/3202; A61M 2005/3267; A61M 5/3271; A61M 5/3243; A61M 5/3269;
(Continued)

(56) References Cited

U.S. PATENT DOCUMENTS

2006/0184134 A1* 8/2006 Heiniger ............... A61M 5/326
604/198
2011/0034879 A1* 2/2011 Crow .................. A61M 5/2033
604/197
(Continued)

FOREIGN PATENT DOCUMENTS

| EP | 2596823 | 5/2013 |
|---|---|---|
| EP | 2944340 | 11/2015 |
| WO | WO 2015/110529 | 7/2015 |

OTHER PUBLICATIONS

International Preliminary Report on Patentability in International Application No. PCT/EP2017/067510, dated Jan. 15, 2019, 8 pages.
(Continued)

Primary Examiner — Emily L Schmidt
(74) Attorney, Agent, or Firm — Fish & Richardson P.C.

(57) ABSTRACT

A drug delivery device includes an inner body adapted to receive a pre-filled syringe with an injection needle, one or more flexible arms on the inner body extending in a distal direction, and one or more support members slidably arranged to operatively outwardly support the flexible arms. The flexible arms have respective inwardly directed protrusions adapted to engage a neck of the syringe. When the support member is in a distal position, it does not support the flexible arms. When the support member is in a proximal position, the support member supports the flexible arms and prevents them from being outwardly deflected.

20 Claims, 5 Drawing Sheets

(52) U.S. Cl.
CPC ........ *A61M 5/3243* (2013.01); *A61M 5/3245* (2013.01); *A61M 5/46* (2013.01); *A61M 2005/2407* (2013.01); *A61M 2005/2437* (2013.01); *A61M 2205/581* (2013.01)

(58) Field of Classification Search
CPC ........ A61M 5/2466; A61M 2005/2474; A61M 5/288; A61M 2005/3235
See application file for complete search history.

(56) References Cited

U.S. PATENT DOCUMENTS

2013/0123711 A1    5/2013  Schoonmaker et al.
2014/0243741 A1    8/2014  Kaufmann et al.

OTHER PUBLICATIONS

International Search Report and Written Opinion in International Application No. PCT/EP2017/067510, dated Sep. 14, 2017, 11 pages.

\* cited by examiner

DRUG DELIVERY DEVICE WITH CONTROLLED NEEDLE SHIELD AND COVER SLEEVE

CROSS REFERENCE TO RELATED APPLICATIONS

The present application is the national stage entry of International Patent Application No. PCT/EP2017/067510, filed on Jul. 12, 2017, and claims priority to Application No. EP 16179492.0, filed on Jul. 14, 2016, the disclosures of which are incorporated herein by reference.

TECHNICAL FIELD

The present disclosure generally relates to a drug delivery device.

BACKGROUND

Administering an injection is a process which presents a number of risks and challenges for users and healthcare professionals, both mental and physical. Pre-filled syringes containing a selected dosage of a medicament for administering the medicament to a patient are known in the art.

There remains a need for an improved drug delivery device.

SUMMARY

An object of the present disclosure is to provide an improved drug delivery device.

The object is achieved by a drug delivery device according to claim 1.

Exemplary embodiments are provided in the dependent claims.

According to the present disclosure, a drug delivery device comprises:
  an inner body adapted to receive a pre-filled syringe with an injection needle,
  one or more flexible arms on the inner body extending in a distal direction, the flexible arms having respective inwardly directed protrusions adapted to engage a neck of the syringe,
  one or more support members slidably arranged to operatively outwardly support the flexible arms,
  wherein, when the support member is in a distal position, it does not support the flexible arms, wherein, when the support member is in a proximal position, the support member supports the flexible arms and prevents them from being outwardly deflected.

This allows for inserting a pre-filled syringe with an attached protective needle sheath in the distal direction into the inner body while the support member is in the distal direction. The protective needle sheath may have an outer diameter substantially equal to an outer diameter of the syringe. During insertion, the protective needle sheath abuts the protrusions on the flexible arms and deflects them outwards so that the protective needle sheath may pass through the protrusions. After having passed the protective needle sheath the protrusions are allowed to relax into a gap between the protective needle sheath and the syringe outside the neck of the syringe thus supporting the neck. If the support member is moved into the proximal position, the flexible arms cannot deflect so a force exerted on the syringe, e.g. a force from a plunger rod acting on a stopper within the syringe, does not result in deflection of the flexible arms and movement of the syringe. Instead, this force is resolved within the inner body and the syringe is in a defined gauge position with a defined needle insertion depth when the support member is in the proximal position due to the protrusions engaging the neck of the syringe.

In an exemplary embodiment a needle cover sleeve is arranged outwardly of the support member, the needle cover sleeve slidable in an axial direction between a distal position and a proximal position to operatively cover or expose the injection needle. This may improve needle safety.

In an exemplary embodiment, when the needle cover sleeve moves from the distal position towards the proximal position, the needle cover sleeve engages and moves the support member from the distal position to the proximal position. The syringe is thus locked in the defined gauge position upon movement of the needle cover sleeve into the proximal position, e.g. upon placement of the drug delivery device against an injection site.

In an exemplary embodiment, the support member comprises an inwardly directed bump adapted to outwardly support the flexible arm, when the support member is in the proximal position. If the bump is axially offset from the flexible arm, the flexible arm is not supported and can thus deflect.

In an exemplary embodiment, an outer body is provided outside the needle cover sleeve, wherein the outer body is coupled with the inner body. The outer body may be gripped by a user for operating the drug delivery device.

In an exemplary embodiment, the needle cover sleeve comprises a dog adapted to engage the support member. In an exemplary embodiment, the dog is adapted to engage the bump on the support member.

In an exemplary embodiment, the outer body comprises an inwardly directed guidance protrusion for outwardly supporting the support member outwardly of the flexible arm. The support member is thus stiffened in the proximal position thus improving prevention of deflection of the flexible arm.

In an exemplary embodiment, the support member is adapted to generate an audible feedback when arriving at the proximal position. This may be used to indicate that the drug delivery device has reached the correct insertion depth during insertion of the needle into the injection site. If the needle cover sleeve is also used to operate an activation mechanism for initiating delivery of a medicament held in the syringe, the audible feedback may also indicate that the injection will start.

In an exemplary embodiment, the support member comprises a hook adapted to engage a latch surface on the body for generating the audible feedback, e.g. a click noise. Furthermore, the support member is thus locked to the body in the proximal position.

In an exemplary embodiment, a ramp and/or a detent are/is arranged on the body adapted to deflect the hook as it moves from the distal position to the proximal position, wherein, when arriving in the proximal position, the previously deflected hook is allowed to relax and engaged the latch surface. This may help to generate the click noise.

In an exemplary embodiment, in the distal position, the hook is distally spaced from the latch surface.

In an exemplary embodiment, the latch surface is arranged on the inner body and the hook is inwardly directed.

In an exemplary embodiment, the protrusions are adapted to engage a gap between a protective needle sheath and the syringe outside a neck of the syringe for supporting the neck to define a gauge position of the needle.

In an exemplary embodiment, in the gauge position, a proximal flange on the syringe is spaced from a proximal end of the inner body.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1:
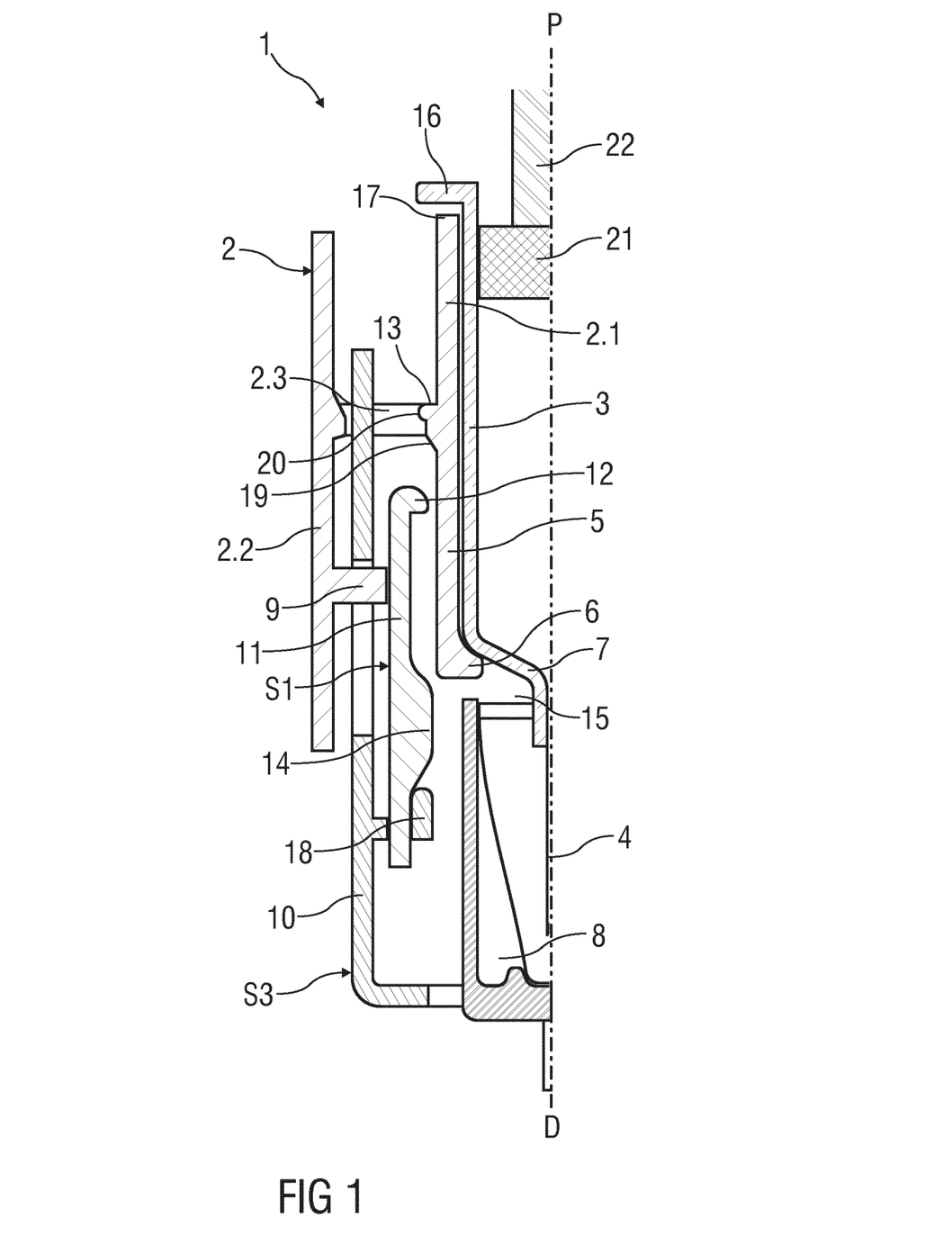
FIG. 1 is a schematic detail view of an exemplary embodiment of a drug delivery device.

FIG. 1 is a schematic detail view of an exemplary embodiment of a drug delivery device 1 comprising a body 2 adapted to receive a pre-filled syringe 3 with an injection needle 4. The body 2 comprises an inner body 2.1 and an outer body 2.2, the inner body 2.1 having one or more flexible arms 5 extending in a distal direction D, the flexible arms 5 having respective inwardly directed protrusions 6 adapted to engage a neck 7 of the syringe 3. In an exemplary embodiment, the flexible body arms 5 may be arranged as half shells. A protective needle sheath 8 may be arranged on the needle 4. The outer body 2.2 is connected to the inner body 2.1 through casework 2.3. The outer body 2.2 comprises an inwardly directed guidance protrusion 9.

A needle cover sleeve 10 is arranged within the outer body 2.2 outwardly of the inner body 2.1, the needle cover sleeve 10 slidable in an axial direction to operatively cover or expose the injection needle 4. One or more support members 11 are slidably arranged between the needle cover sleeve 10 and the inner body 2.1 to operatively outwardly support the flexible arms 5. The support member 11 may be arranged as a sleeve or as a beam. The support member 11 comprises a hook 12 at a proximal end adapted to engage a latch surface 13 on the body 2. In the illustrated embodiment, the latch surface 13 is arranged on the inner body 2.1 and the hook 12 is inwardly directed. In other embodiments, the latch surface 13 could be arranged on another part of the body 2 and the hook 12 could be outwardly directed. The support member 11 furthermore comprises an inwardly directed bump 14 adapted to outwardly support the flexible arm 5. The support member 11 has a distal position S1 as shown in FIG. 1, in which the bump 14 is arranged distally from the flexible arms 5 so that they can outwardly deflect. Furthermore, in the distal position S1, the hook 12 is distally spaced from the latch surface 13 and thus not engaged to the body 2. The guidance protrusion 9 outwardly supports the support member 11. The needle cover sleeve 10 is also in a distal position S3. A dog 18 on the needle cover sleeve 10 engages the support member 11, e.g. the bump 14 of the support member 11, such that upon movement of the needle cover sleeve 10 in a proximal direction P the support member 11 would also be moved in the proximal direction P.

In an exemplary embodiment, a sheath remover (not illustrated) may be arranged to engage the protective needle sheath 8 so that upon removal of the shield remover from the drug delivery device 1, the protective needle sheath 8 is also removed. The sheath remover may be part of a cap for covering the distal end of the drug delivery device 1.

Figure 2:
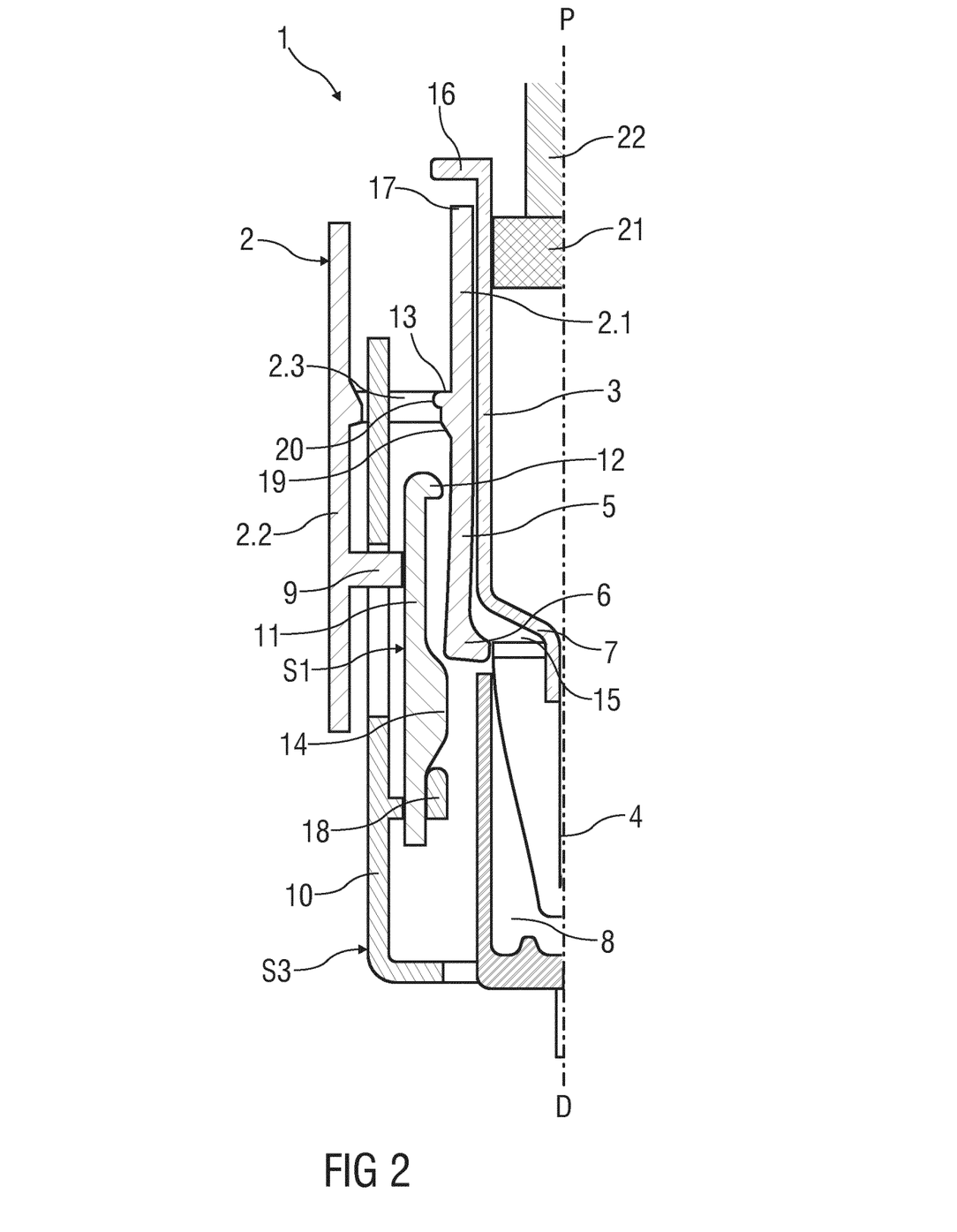
FIG. 2 is a schematic detail view of the drug delivery device during insertion of a syringe.

FIG. 2 is a schematic detail view of the drug delivery device 1 during assembly as a syringe 3 with an attached protective needle sheath 8 is inserted into the inner body 2.1 in the distal direction D. The protective needle sheath 8 may have an outer diameter substantially equal to an outer diameter of the syringe 3. In this assembly step, the support member 11 is in the distal position S1 so that the flexible arms 5 are not outwardly supported and may thus deflect. The needle cover sleeve 10 is in the distal position S3.

During insertion, the protective needle sheath 8 abuts the protrusions 6 on the flexible arms 5 and deflects them outwards so that the protective needle sheath 8 may pass through the protrusions 6. After having passed the protective needle sheath 8 the protrusions 6 are allowed to relax into a gap 15 between the protective needle sheath 8 and the syringe 3 outside the neck 7 of the syringe 3 thus supporting the neck 7 so that the syringe 3 is in an axial position in which a proximal flange 16 on the syringe 3 is still spaced from a proximal end 17 of the inner body 2.1.

Figure 3:
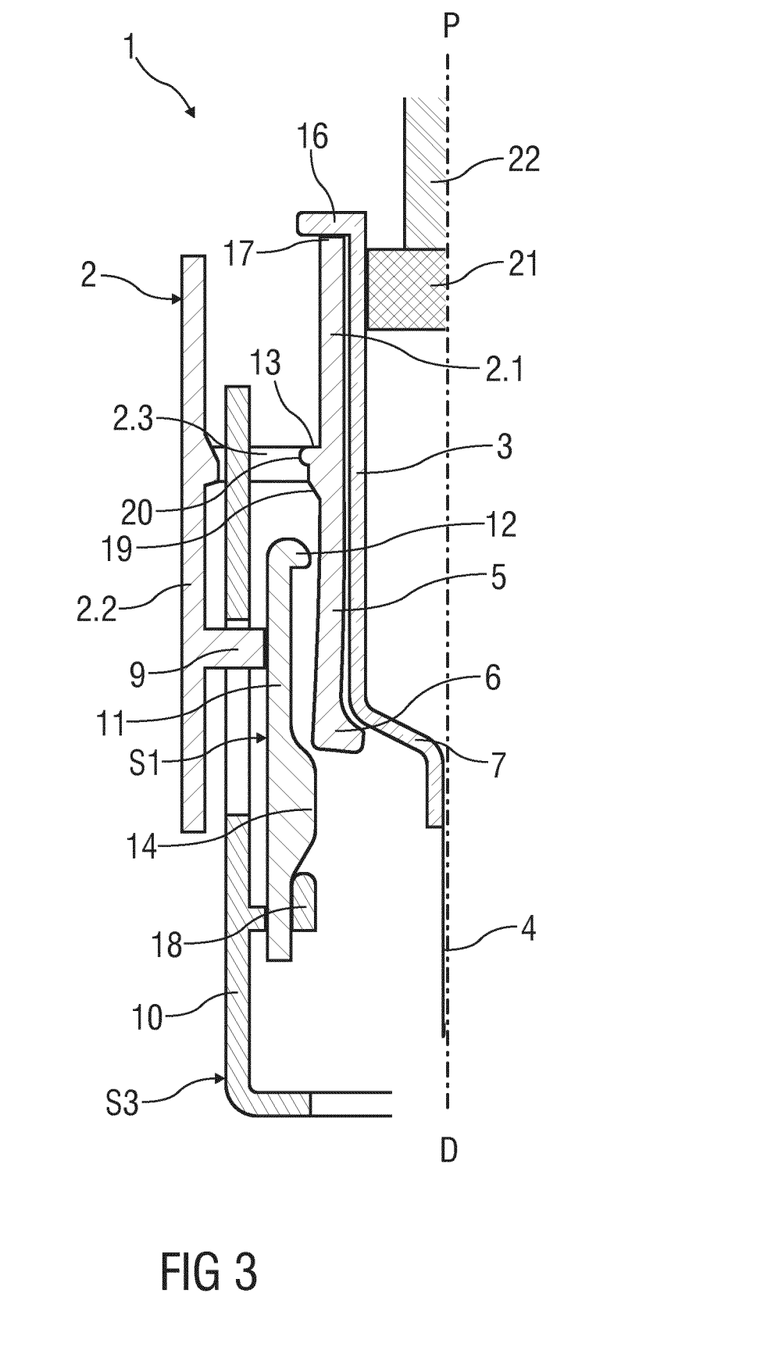
FIG. 3 is a schematic detail view of the drug delivery device during removal of a protective needle sheath.

FIG. 3 is a schematic detail view of the drug delivery device 1 during removal of the protective needle sheath 8 by pulling the protective needle sheath 8 or a sheath remover engaged with the protective needle sheath 8 in the distal direction D. As the protective needle sheath 8 is frictionally engaged to the neck 7 of the syringe 3, this movement also moves the syringe 3 so that the syringe 3 engages the protrusions 6 and slightly deflects the flexible arms 5 until the proximal flange 16 abuts the proximal end 17 of the inner body 2.1. At this point, movement of the syringe 3 in the distal direction D stops and further movement of the needle sheath 8 pulls it off the neck 7 and needle 4. A force which has to be resolved by the body 2 in the distal direction D in this situation is thus limited to the amount of force required to remove the protective needle sheath 8 from the syringe 3. After removal of the protective needle sheath 8 or after the friction force holding the protective needle sheath 8 on the neck 7 is overcome, the flexible arms 5 relax inwards and the protrusions 6 move the syringe 3 back in the proximal direction P such that the proximal flange 16 is again spaced from the proximal end 17 of the inner body 2.1 (not shown). The syringe 3 thus arrives in a correct gauge position resulting in a correct needle insertion depth during injection.

Figure 4:
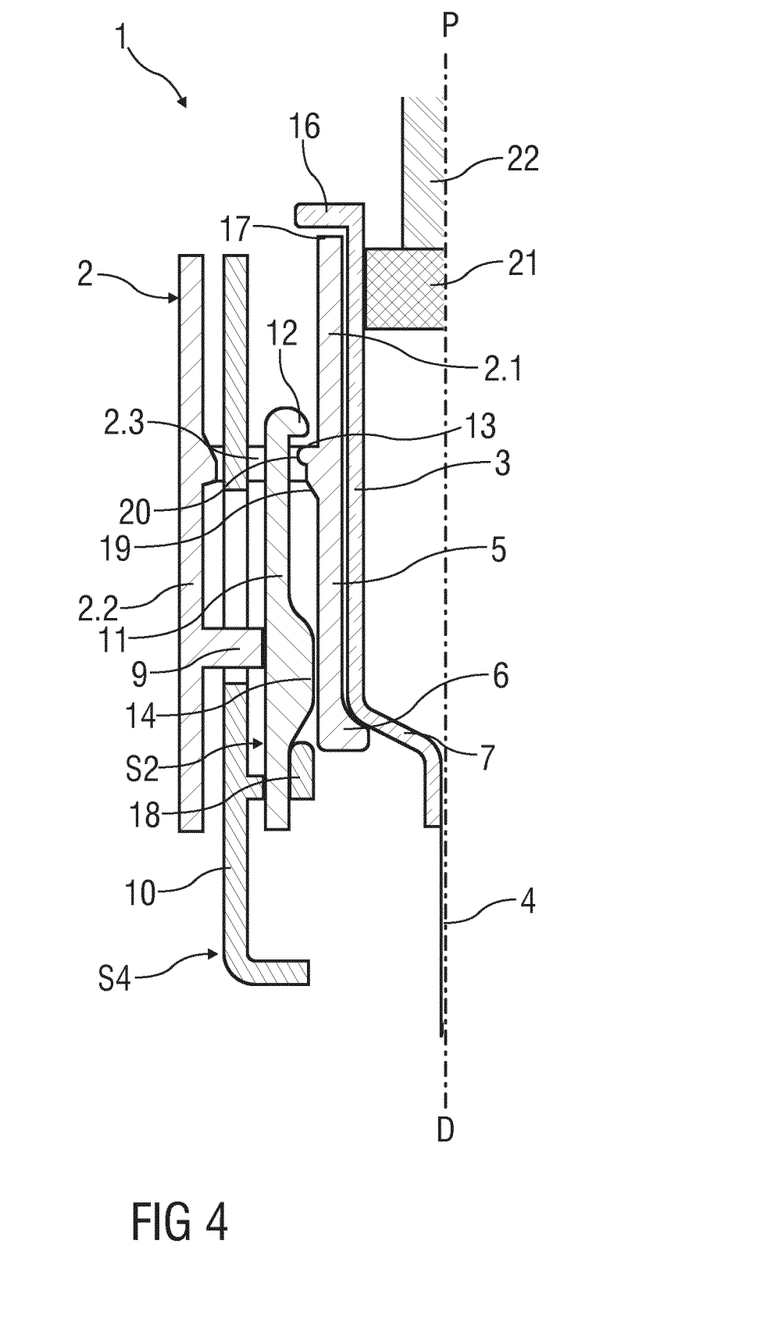
FIG. 4 is a schematic detail view of the drug delivery device during needle insertion.

FIG. 4 is a schematic detail view of the drug delivery device 1 during needle insertion. The drug delivery device 1 is held on the outer body 2.2 and the needle cover sleeve 10 is pushed against an injection site, e.g. a patient's skin. Consequently, the needle cover sleeve 10 moves from the distal position S3 in the proximal direction P into a proximal position S4 thus exposing the needle 4 and allowing it to pierce the injection site. Due to the engagement of the dog 18 of the needle cover sleeve 10 to the support member 11, the movement of the needle cover sleeve 10 has also caused movement of the support member 11 in the proximal direction P into a proximal position S2 such that the bump 14 is now located radially outwardly of the flexible arms 5 so that they cannot be deflected any more. The guidance protrusion 9 on the outer body 2.2 outwardly supports the support member 11 radially outwardly of the bump 14 thus stiffening the support member 11. Furthermore, during movement of the support member 11 in the proximal direction P, the hook 12 has been deflected by a ramp 19 and a detent 20 on the inner body 2.1 and, when arriving in the proximal position S2, the hook 12 has relaxed and engaged the latch surface 13 such that the support member 11 is locked to the inner body 2.1 in the proximal position S2. As the hook 12 relaxes and engages the latch surface 13, an audible feedback such as a click noise may be generated informing the user that the needle 4 has reached insertion depth. The drug delivery device 1 may comprise an activation mechanism (not shown) initiating displacement of a stopper 21 within the syringe 3 by a plunger rod 22 to inject a medicament held in the syringe 3 at this point such that the audible feedback also indicates the start of injection. During injection a force is exerted by the plunger rod 22 on the stopper 21. This force is at least partially resolved by the inner body 2.1 through the syringe 3 and the protrusions 6 on the flexible arms 5. As the flexible arms 5 cannot deflect any more, the axial position of the syringe 3 and the needle 4 is defined by the protrusions 6 engaging the syringe 3. This ensures the correct insertion depth of the needle 4. Supporting the syringe 3 at the neck 7 rather than at the more fragile proximal flange 16 reduces the risk of damaging the syringe 3.

Figure 5:
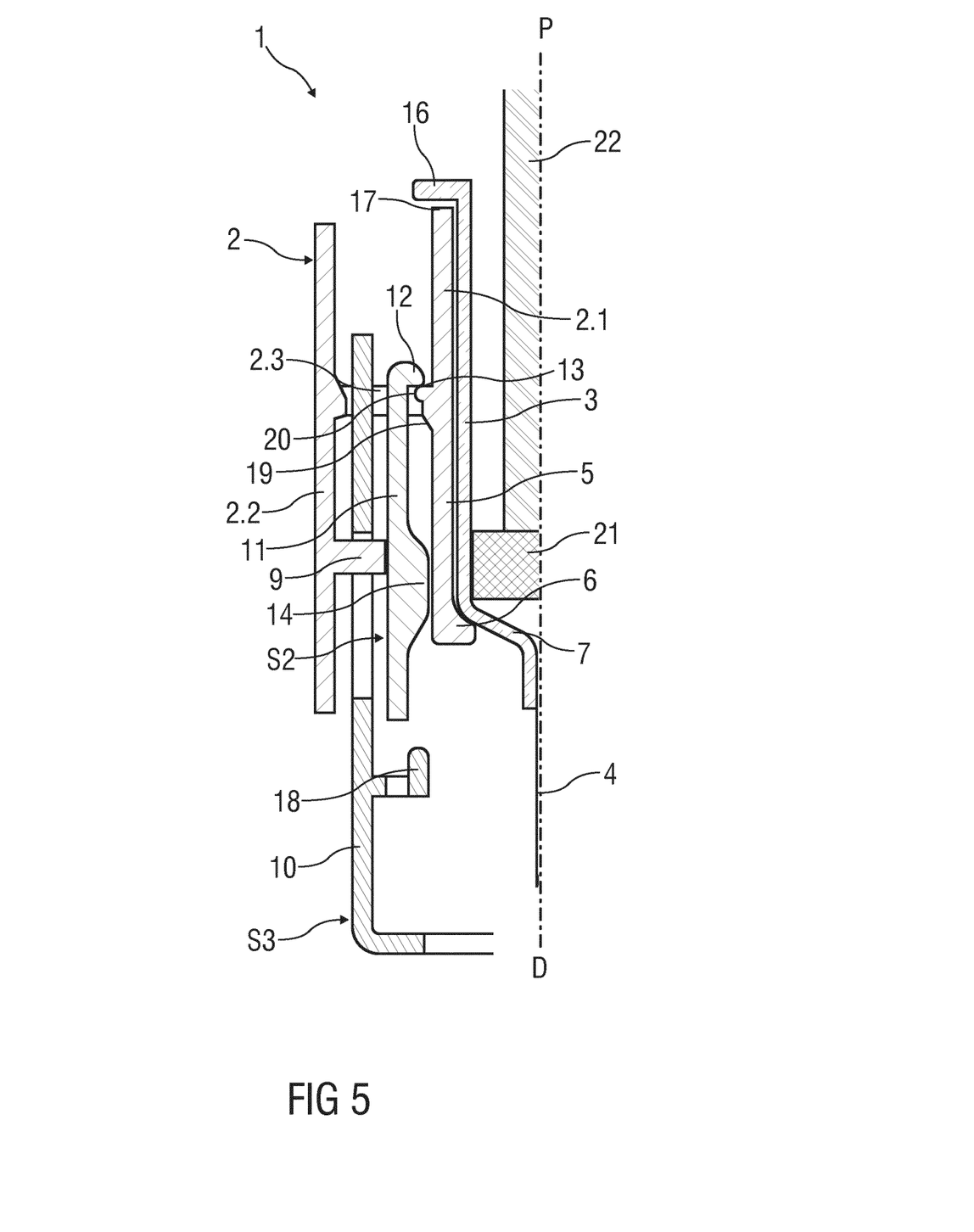
FIG. 5 is a schematic detail view of the drug delivery device with an extended needle cover sleeve.

FIG. 5 is a schematic detail view of the drug delivery device 1 with the needle cover sleeve 10 in the distal position S3. After injection of the medicament, the drug delivery device 1 may be removed from the injection site. The needle cover sleeve 10 may thus move or be moved in the distal direction D again, e.g. pulled by a user or driven by a needle sleeve spring (not shown). A locking mechanism (not shown) may be arranged to lock the needle cover sleeve 10 in the distal position S3 after injection. The support member 11 does not return to its distal position S1 as it is coupled to the inner body 2.1 by the hook 12 and the latch surface 13.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle 4, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoylgamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
2 body
2.1 inner body
2.2 outer body
2.3 casework
3 syringe 4 needle
5 flexible arm
6 protrusion
7 neck
8 protective needle sheath
9 guidance protrusion
10 needle cover sleeve
11 support member
12 hook
13 latch surface
14 bump
15 gap
16 proximal flange
17 proximal end
18 dog
19 ramp
20 detent
21 stopper
22 plunger rod
D distal direction
P proximal direction
S1 distal position
S2 proximal position
S3 distal position
S4 proximal position

The invention claimed is:

1. A drug delivery device, comprising:
an inner body adapted to receive a pre-filled syringe with an injection needle;
one or more flexible arms on the inner body extending in a distal direction, the one or more flexible arms having respective inwardly directed protrusions adapted to engage a neck of the syringe; and
a support member configured to slide in a proximal direction from a distal position to a proximal position relative to the one or more flexible arms, wherein the support member is slidably arranged to operatively outwardly support the one or more flexible arms,
wherein, when the support member is in the distal position, the support member does not support the one or more flexible arms, and wherein, when the support member is in the proximal position, the support member supports the one or more flexible arms and prevents the one or more flexible arms from being outwardly deflected.

2. The drug delivery device according to claim 1, wherein the support member comprises an inwardly directed bump adapted to outwardly support the one or more flexible arms when the support member is in the proximal position.

3. The drug delivery device according to claim 1, wherein the protrusions are adapted to engage a gap between a protective needle sheath and the syringe outside the neck of the syringe for supporting the neck to define a gauge position of the injection needle.

4. The drug delivery device according to claim 3, wherein in the gauge position a proximal flange on the syringe is spaced from a proximal end of the inner body.

5. The drug delivery device according to claim 1, wherein the support member is adapted to generate an audible feedback when arriving at the proximal position.

6. The drug delivery device according to claim 5, wherein the support member comprises a hook adapted to engage a latch surface on the inner body or an outer body of the drug delivery device.

7. The drug delivery device according to claim 6, wherein a ramp is arranged on the inner body or the outer body, the ramp adapted to deflect the hook of the support member as the support member moves from the distal position to the proximal position, wherein, when arriving in the proximal position, the hook is allowed to relax and engage the latch surface.

8. The drug delivery device according to claim 6, wherein a detent is arranged on the inner body or the outer body, the detent adapted to deflect the hook of the support member as the support member moves from the distal position to the proximal position, wherein, when arriving in the proximal position, the hook is allowed to relax and engage the latch surface.

9. The drug delivery device according to claim 6, wherein a ramp and a detent are arranged on the inner body or the outer body, the ramp and the detent adapted to deflect the hook of the support member as the support member moves from the distal position to the proximal position, wherein, when arriving in the proximal position, the hook is allowed to relax and engage the latch surface.

10. The drug delivery device according to claim 6, wherein, when the support member is in the distal position, the hook is distally spaced from the latch surface.

11. The drug delivery device according to claim 6, wherein the latch surface is arranged on the inner body, and the hook is inwardly directed.

12. The drug delivery device according to claim 1, wherein a needle cover sleeve is arranged outwardly of the support member, the needle cover sleeve slidable in an axial direction between a distal position and a proximal position to operatively cover or expose the injection needle.

13. The drug delivery device according to claim 12, wherein, when the needle cover sleeve moves from the distal position towards the proximal position, the needle cover sleeve engages and moves the support member from the distal position to the proximal position.

14. The drug delivery device according to claim 12, wherein an outer body is provided outside the needle cover sleeve, wherein the outer body is coupled with the inner body.

15. The drug delivery device according to claim 14, wherein the outer body comprises an inwardly directed guidance protrusion for outwardly supporting the support member outwardly of the one or more flexible arms.

16. The drug delivery device according to claim 12, wherein the needle cover sleeve comprises a dog adapted to engage the support member.

17. The drug delivery device according to claim 16, wherein the dog is adapted to engage a bump of the support member.

18. The drug delivery device according to claim 1, wherein the support member comprises a plurality of support members.

19. The drug delivery device according to claim 1, wherein the inner body is adapted to engage an outer surface of the syringe.

20. A drug delivery device, comprising:
an inner body adapted to receive a pre-filled syringe with an injection needle;
one or more flexible arms on the inner body extending in a distal direction, the one or more flexible arms having respective inwardly directed protrusions adapted to engage a neck of the syringe;
a support member slidably arranged to operatively outwardly support the one or more flexible arms; and
a needle cover sleeve arranged outwardly of the support member, the needle cover sleeve slidable in an axial direction between a distal position and a proximal position to operatively cover or expose the injection needle, wherein, when the support member is in a distal position, the support member does not support the one or more flexible arms, and wherein, when the support member is in a proximal position, the support member supports the one or more flexible arms and prevents the one or more flexible arms from being outwardly deflected, and wherein, when the needle cover sleeve moves from the distal position towards the proximal position, the needle cover sleeve engages and moves the support member from the distal position to the proximal position.

* * * * *